United States Patent [19]

Stark et al.

[11] Patent Number: 5,413,000
[45] Date of Patent: May 9, 1995

[54] ASSEMBLY FOR REMOVING WASTE FROM CLOSED SAMPLE CONTAINERS

[75] Inventors: William A. Stark, Costa Mesa; Kenneth R. Rogers, Redlands; Antoine E. Haddad, El Toro, all of Calif.

[73] Assignee: Dade International Inc., Deerfield, Ill.

[21] Appl. No.: 918,929

[22] Filed: Jul. 22, 1992

Related U.S. Application Data

[63] Continuation of Ser. No. 655,248, Feb. 13, 1991, abandoned, which is a continuation of Ser. No. 376,714, Jul. 7, 1989, abandoned, which is a continuation-in-part of Ser. No. 210,695, Jun. 23, 1988, Pat. No. 4,951,512.

[51] Int. Cl.⁶ ............................................. G01N 1/00
[52] U.S. Cl. .................................................. 73/864.23
[58] Field of Search .................. 73/864.21–864.25, 73/864.86, 864.87, 864.23; 422/100, 63, 64

[56] References Cited

U.S. PATENT DOCUMENTS

| | | | |
|---|---|---|---|
| 1,930,182 | 10/1933 | Richardson | 152/12 |
| 2,256,656 | 9/1941 | Swabacker | 128/214 |
| 2,503,147 | 4/1950 | Applezweig | 226/116 |
| 2,584,397 | 2/1952 | Pitman | 226/116 |
| 2,689,562 | 9/1954 | Adams et al. | 128/214 |
| 2,855,929 | 10/1958 | Hein, Jr. | 128/221 |
| 3,719,086 | 3/1973 | Bannister et al. | 73/864.22 |
| 3,817,090 | 6/1974 | Michel | 73/81 |
| 3,872,730 | 3/1975 | Ringrose et al. | 73/864.22 |
| 3,900,289 | 8/1975 | Liston | 23/230 R |
| 3,991,627 | 11/1976 | Laird et al. | 73/423 R |
| 4,046,511 | 9/1977 | Stabile | 33/16 |
| 4,080,833 | 3/1978 | Huber | 73/423 |
| 4,106,701 | 8/1978 | Siefken | 239/271 |
| 4,120,662 | 10/1978 | Fosslien | 73/864.24 |
| 4,123,173 | 10/1978 | Bullock et al. | 356/246 |
| 4,143,658 | 3/1979 | Rambosek et al. | 128/184 |
| 4,166,094 | 8/1979 | Froehlich et al. | 422/64 |
| 4,180,071 | 12/1979 | Oiwa | 128/218 N |
| 4,203,443 | 5/1980 | Genese | 128/272.3 |
| 4,210,724 | 7/1980 | Sogi et al. | 435/292 |
| 4,215,690 | 8/1980 | Oreopoulos et al. | 128/221 |

(List continued on next page.)

FOREIGN PATENT DOCUMENTS

| | | |
|---|---|---|
| 42036 | 12/1981 | European Pat. Off. . |
| 0061317 | 9/1982 | European Pat. Off. . |
| 41378 | 12/1984 | European Pat. Off. . |
| 275119 | 7/1988 | European Pat. Off. . |
| 355823 | 2/1990 | European Pat. Off. . |
| 2600299 | 7/1976 | Germany . |
| 2218569 | 4/1979 | Germany .......... 73/864.22 |
| 2095403 | 9/1982 | United Kingdom . |
| 8904955 | 6/1989 | WIPO . |
| 8912829 | 12/1989 | WIPO . |

OTHER PUBLICATIONS

How To Use The CleanTech System, 4 page pamphlet from CleanTech, published Nov. 1988.

(List continued on next page.)

*Primary Examiner*—Robert Raevis
*Attorney, Agent, or Firm*—Mark J. Buonaiuto

[57] ABSTRACT

The present invention provides a waste removal assembly used in conjunction with a sampling system which provides access to a sealed container. The assembly includes a lifting mechanism which moves a sample container against a hollow cleaning needle. The needle penetrates the stopper of the container, and its penetrating end moves into the container proximate the inside surface of the stopper. The assembly also includes a pump and tube arrangement in communication with the needle for removing or displacing entrapped serum or other debris from the bottom surface of the stopper and placing it in a waste container. After removing the debris from the container, the cleaning assembly vents the cleaned container to atmospheric pressure, and the sampling system performs sampling operations through a puncture tube which defines a temporary opening in the stopper of the container.

6 Claims, 8 Drawing Sheets

U.S. PATENTS DOCUMENTS

| | | | |
|---|---|---|---|
| 4,235,840 | 11/1980 | Mendoza et al. | 422/64 |
| 4,298,570 | 11/1981 | Lillig et al. | 422/64 |
| 4,340,390 | 7/1982 | Collins et al. | 23/230 B |
| 4,477,190 | 10/1984 | Liston et al. | 356/418 |
| 4,478,095 | 10/1984 | Bradley et al. | 73/864.21 |
| 4,478,958 | 10/1984 | Carlson et al. | 264/53 |
| 4,484,483 | 11/1984 | Riegger et al. | 73/846.23 |
| 4,528,159 | 7/1985 | Liston | 422/65 |
| 4,595,562 | 6/1986 | Liston et al. | 422/65 |
| 4,647,432 | 3/1987 | Wakatake | 422/64 |
| 4,662,231 | 5/1987 | Schoorschmidt et al. | 73/864.23 X |
| 4,665,758 | 5/1987 | Schoorschmidt | 73/864.23 X |
| 4,669,321 | 6/1987 | Meyer | 73/863.85 |
| 4,703,762 | 11/1987 | Rathbone et al. | 128/763 |
| 4,713,974 | 12/1987 | Stone | 73/864.21 |
| 4,721,137 | 1/1988 | Muller | 141/65 |
| 4,743,243 | 5/1988 | Vaillancourt | 604/166 |
| 4,756,201 | 7/1988 | Uffenheimer | 73/864.21 |
| 4,788,871 | 12/1988 | Nelson et al. | 73/866.5 |

OTHER PUBLICATIONS

*Factors Influencing The Coring Of Rubber Closures*, G. H. Hopkins, Oct. 15, 1958; Technical Report No. 9, 6 pages.

*Coring: The Unseen Menace*, Peter A. Charlebois, B.SC., M. D., Can. Anaes. Soc. J., vol. 13, No. 6, Nov., 1966, pp. 585–597.

*New Developments In Hypodermic Needles*, Brian E. Baldwin, Bulletin of the Parenteral Drug Association, Nov.–Dec., 1971, vol. 25, No. 6, pp. 275–278.

*Purchasing Digest/Needle Sharpness*, N. J. Menolasino, Ph.D. and H. H. Hetz, M.D.; 2 pages.

*The Mechanism of Aging of Elastomers: I. Modes of Degradation and Protective Measures*, George H. Hopkins and Frank M. Keim, Bulletin, of the Parenteral Drug Association, Jul.–Aug., 1977, vol. 31, No. 4, pp. 201–210.

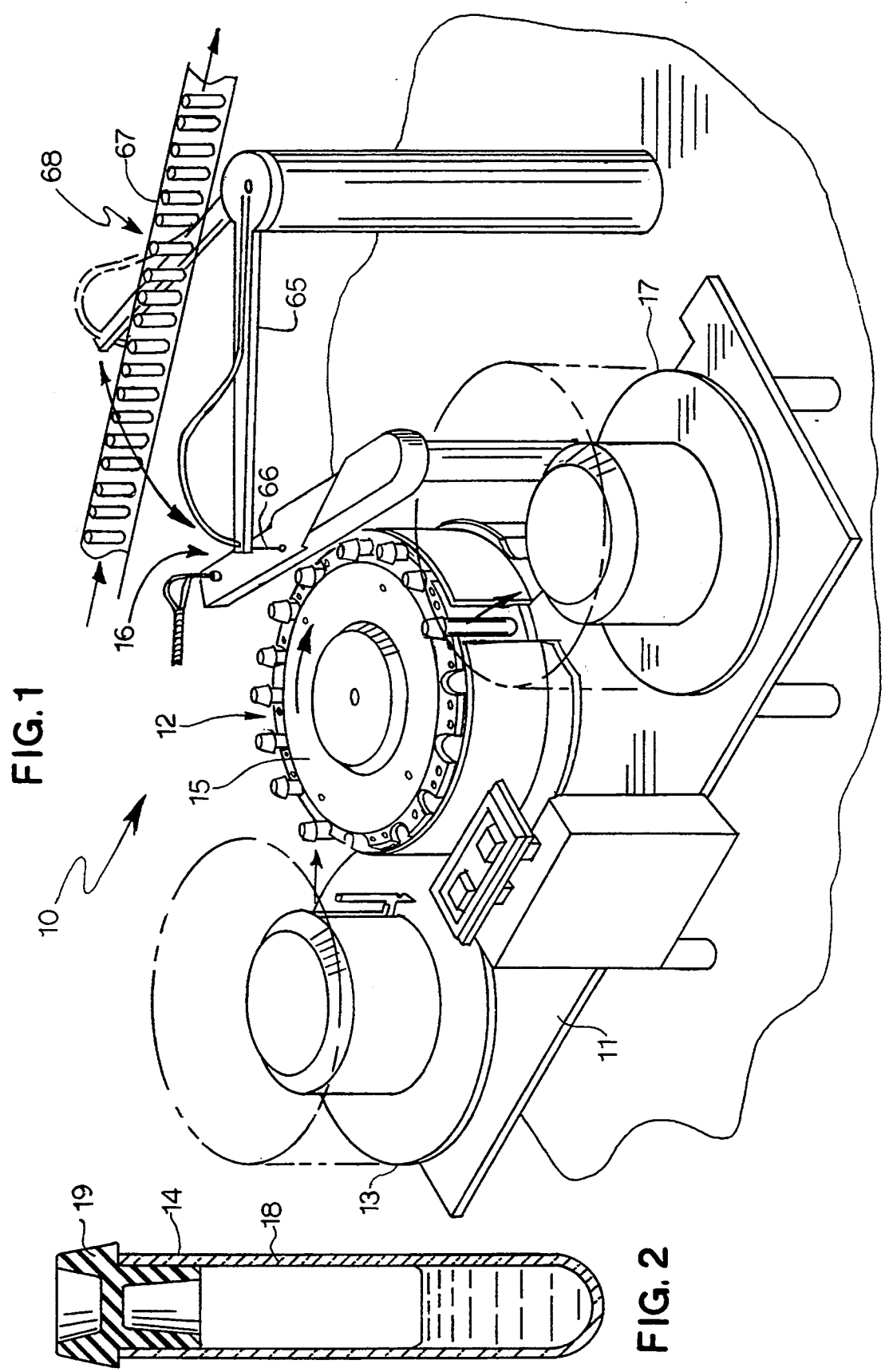

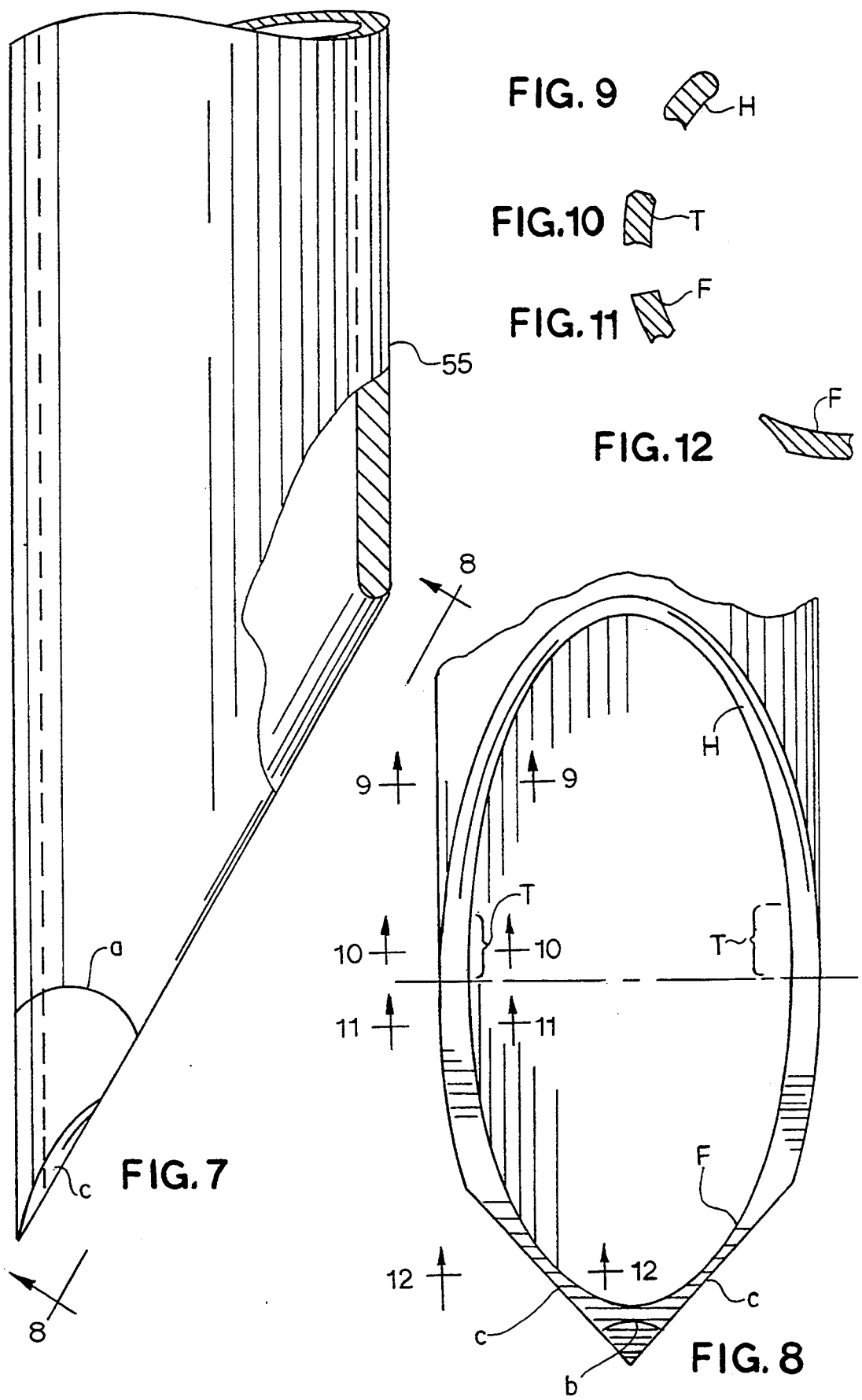

ASSEMBLY FOR REMOVING WASTE FROM CLOSED SAMPLE CONTAINERS

This application is a continuation of application Ser. No. 376,714, filed Jul. 7, 1989, now abandoned. This application is a continuation of application Ser. No. 655,248, filed Feb. 13, 1991, now abandoned. This application is a continuation-in-part of application Ser. No. 210,695, filed Jun. 23, 1988, (now U.S. Pat. No. 4,951,512) for a "System for Providing Access to Sealed Containers."

BACKGROUND OF THE INVENTION

1. Field of the Invention

The present invention generally relates to an assembly for removing or displacing waste from the inside of a closed sample container, and more particularly to a waste removal assembly used in conjunction with an automatic sampler system which provides a temporary opening in the closure of a sample container.

2. Description of the Prior Art

The prior art provides a number of automatic sampling systems. Generally, these systems receive sample containers, remove a predetermined quantity of sample from each container at a first location, and transfer the removed sample to a second location for analysis. The sample containers usually used with these systems are open-top vials or tubes transported in the system on carousels and transferred between carousels with mechanical push-arms and other similar devices.

Using open sample containers in an automatic sampling system presents a number of problems. First, the various forces which move the container through the system may cause spills and contamination. Second, open sample containers may expose an operator to any harmful substances disposed in the containers. Finally, because open containers require special care, the cost of operation increases.

One solution to these problems is to use closed containers in an automated system which can form a temporary opening in the stopper of a closed container. However, using this system presents other problems. Specifically, the sample in the container, e.g., blood serum, may splash against the side of the container and on the bottom of the container stopper in response to operator handling and/or movements of the container in the system. Some of the sample which contacts the bottom of the stopper may adhere to the stopper and may contaminate the puncture tube which provides a temporary opening through which the system conducts sampling operations.

Thus, a through the stopper sampling system must include means for removing any sample or debris from the bottom of the stopper and the surrounding area immediately before the system moves the puncture tube through the stopper. It must remove this debris quickly and efficiently; and it must do so through the stopper without removing the stopper.

The waste removal assembly of the present invention used in conjunction with a through the stopper sampling system fulfills the above requirements. It is a simple and fully automated assembly which minimizes the expense of manufacture and assembly and gives precise, uniform, and reliable performance. It allows the automated sampling system to remove waste from the bottom of the stopper and the surrounding area of each sample tube before the system performs sampling operations through the stopper.

SUMMARY OF THE INVENTION

In accordance with one embodiment of this invention, a waste removal assembly includes a hollow needle means with an open, first end secured to a needle support member and a second, distal end defining a sharp point and including at least one opening. Passageway means connects the first end of the needle means to a pump. The pump removes, through the passageway means, any material in the needle means or any material proximate the opening at the sharp, second end of the needle means. The pump also moves the debris from the passageway means to a waste disposal container.

A lift means disposed proximate the needle means receives a sample container and moves the stopper of the container against the needle means. The lift means provides the force required for puncturing the stopper with the needle; and it moves the container a predetermined distance so that the needle means extends through the stopper and into the container. In this position, the opening at the second, sharp end of the needle lies proximate the inner surface of the container stopper where it may remove debris adhered to the surface. Alternatively, the sample container may remain stationery and the needle support member may move the needle into and through the stopper of the container.

A carousel (or any other suitable transport means) in an automated sampling system moves the sample containers to a first location where the lifting means receives two adjacent or consecutive sample containers. It lifts the two containers simultaneously, a first one against the needle means and the other, second container against a hollow puncture tube. The lift means continues to lift the two containers until the needle means punctures the stopper of the first container and extends into the first container and until the puncture tube punctures the stopper of the second container and extends into the second container.

When the lift means stops lifting, the puncturing end of the needle means lies proximate the inside surface of the stopper of the first container. There, the needle means removes debris from the bottom of the stopper. Then, a vent means vents the first container through the needle means and brings the sample in this container to atmospheric pressure.

When the lift means stops lifting, the puncturing end of the puncture tube lies proximate the stopper a predetermined distance above the sample in the second container. The puncturing end of the tube is bevelled with a sharpened lower most portion and a rounded and polished heel which facilitate penetration without coring the stopper. While the system removes waste material from the first container, it performs sampling operations through the puncture tube, i.e., it removes a sample from the second container, places sample into the second container, or senses the properties of the sample in the second container.

After completion of the operations described above, a stripper means disengages the containers from the needle means and from the puncture tube and moves them back onto the carousel. The carousel then moves the cleaned first container to the position previously occupied by the sampled second container. Thus, each incremental rotation of the carousel brings a container from the cleaning position to the sampling position.

BRIEF DESCRIPTION OF THE DRAWINGS

For a more complete understanding of this invention, one should now refer to the embodiment illustrated in greater detail in the accompanying drawings and described below by way of an example of the invention. In the drawings:

FIG. 1 is a perspective view of an automated sampling system which includes the waste removal assembly of the present invention.

FIG. 2 is a sectional view of a sample container of a type used in the sampling system of FIG. 1.

FIG. 7 is a partial side elevation view of the puncture tube used in the automated, through-the-stopper sampling system shown in FIG. 1.

FIG. 8 is an auxiliary elevation view of the puncturing end or face of the puncture tube.

FIG. 9 is a partial cross-sectional view taken along line 9—9 in FIG. 8.

FIG. 10 is a partial cross-sectional view taken along line 10—10 in FIG. 8.

FIG. 11 is a partial cross-sectional view taken along line 11—11 in FIG. 8.

FIG. 12 is a partial cross-sectional view taken along line 12—12 in FIG. 8.

Figure 3:
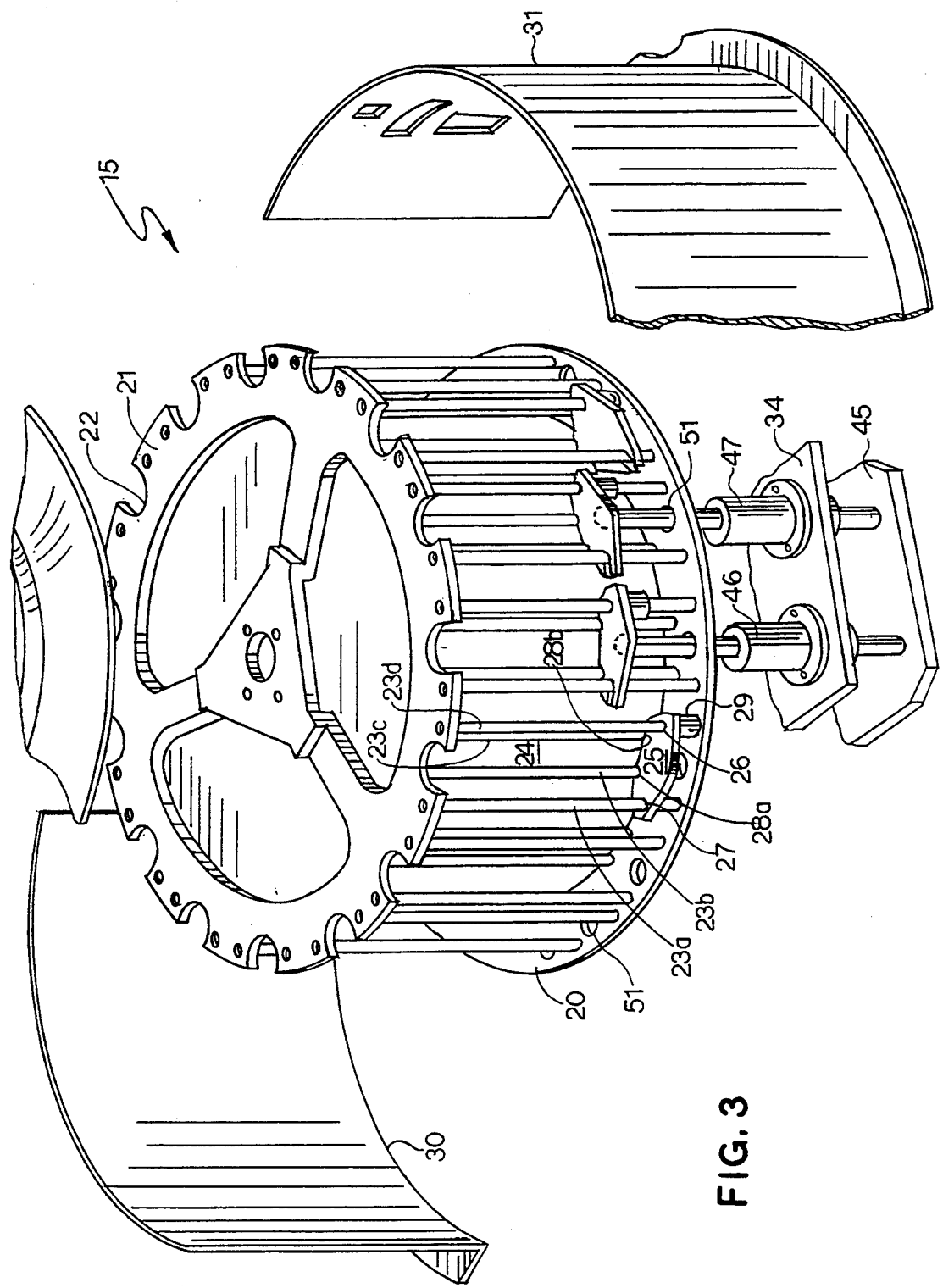
FIG. 3 is a partial, exploded view of the carousel which holds the sample containers which the system samples.

While the drawings and the specification will describe the invention in connection with a preferred embodiment, one should understand that the invention is not limited to this embodiment. Furthermore, one should understand that the drawings are not to scale and that the embodiment is illustrated by graphic symbols, diagrammatic representations and fragmentary views. In certain instances, the applicants may have omitted details which are not necessary for an understanding of the present invention, such as conventional details of fabrication and assembly.

DETAILED DESCRIPTION OF THE DRAWINGS AND A PREFERRED EMBODIMENT

Turning now to the drawings, FIG. 1 illustrates an automatic sampling system at 10. This system includes a base plate 11 for supporting a carousel assembly 12, including a loading carousel 13 which provides closed sample containers 14 to the system, a transfer carousel 15 for receiving the sample containers 14 from the loading carousel 13 and moving them to a first location 16, and an unloading carousel 17 which receives the containers from the transfer carousel 15 and stores them for retrieval by an operator. Liston et al. U.S. Pat. No. 4,595,562 entitled "Loading and Transfer Assembly for Chemical Analyzer" discloses the carousel assembly 12 in greater detail. With this reference, the applicants incorporate the disclosure of that patent to the disclosure of the present application.

The closed container 14 used with the system 10 and shown in FIG. 2 is preferably a glass tube 18 with an open top and a stopper 19 which normally closes the top opening. In addition, the stopper 19 is a self-sealing material, e.g., rubber, which can hermetically close a small slit or hole made in it by a slender puncture tube or needle. Alternatively, the system 10 may use containers of any suitable shape made of any suitable fluid-tight material. Also, the closure may be any suitable device with components which allow a penetrating member to displace them and define an opening through the closure, as described below.

The transfer carousel 15 (See FIG. 3) includes a bottom plate 20 with a flat, ring-like configuration. It also includes a top plate 21 which has the shape of a spoke wheel with semi-circular slots 22 formed in its periphery. The spacing between these slots is constant, and their size and shape generally coincides with the cross-sectional dimensions of the sample container 14 used with the system 10. A post 23a, two rollers 23b and 23c, and a post 23d disposed vertically around each slot and between the bottom plate 20 and the top plate 21 define a compartment 24 for receiving a container 14. Each one of the posts 23a and 23d lies fixedly secured at one end to the plate 20 and at its other end to the plate 21. Similarly, each one of the rollers 23b and 23c lies rotatably mounted at one of its ends to the plate 20 and at the other end to the plate 21.

Each compartment 24 contains a platform member 25 which supports a sample container 14. This platform 25 is a flat, horizontal member with an opening 26 through which the post 23d extends, in sliding engagement with the platform. In addition, the platform 25 has one guide slot 27 and clearance slots 28a and 28b formed around its periphery. The slot 27 co-acts with the post 23a to maintain the platform in alignment in the compartment 24. Finally, the platform 25 includes a guide sleeve 29 secured to the bottom of the platform member 25 and disposed around the post 23d, in sliding engagement with the post 23d, to further maintain the platform in alignment.

Two cover plates 30 and 31 close the compartments 24 around the periphery of the transfer carousel 15, except at the location where the transfer carousel 15 receives a container from the loading carousel 13 and where it transfers the container to the unloading carousel 17. Suitable connecting devices secure these plates 30 and 31 to the base plate 11 around the transfer carousel. These plates do not contact the transfer carousel 15;

they merely prevent the containers 14 from falling out of their compartments 24.

Figure 4:
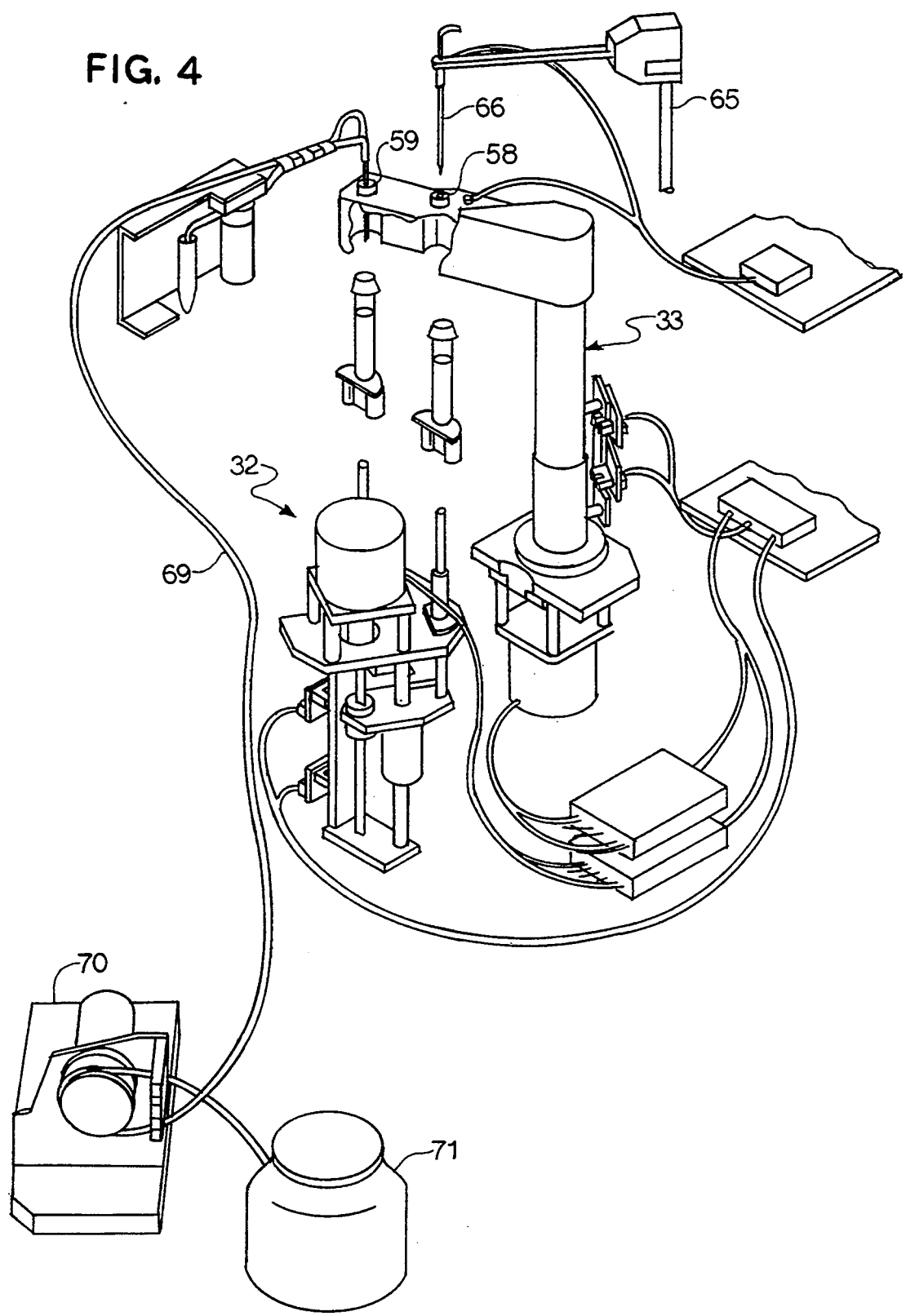
FIG. 4 is a schematic view of the waste removal assembly of the present invention.

A lift mechanism 32 and a puncturing mechanism 33, disposed at the first location 16 (See FIG. 4), temporarily open the closure or stopper 19 of two consecutive or adjacent containers 14 placed there by the transfer carousel 15. The lift mechanism 32 drives two adjacent platforms 25 disposed at the first location and raises the containers 14 from a lowered position to a raised position. As the lifting mechanism 32 lifts the two containers 14, the puncturing mechanism 33 receives them and forms a temporary opening in the stoppers 19 of each container using the force provided by the lifting mechanism 32, as described below.

Figures 5, 15:
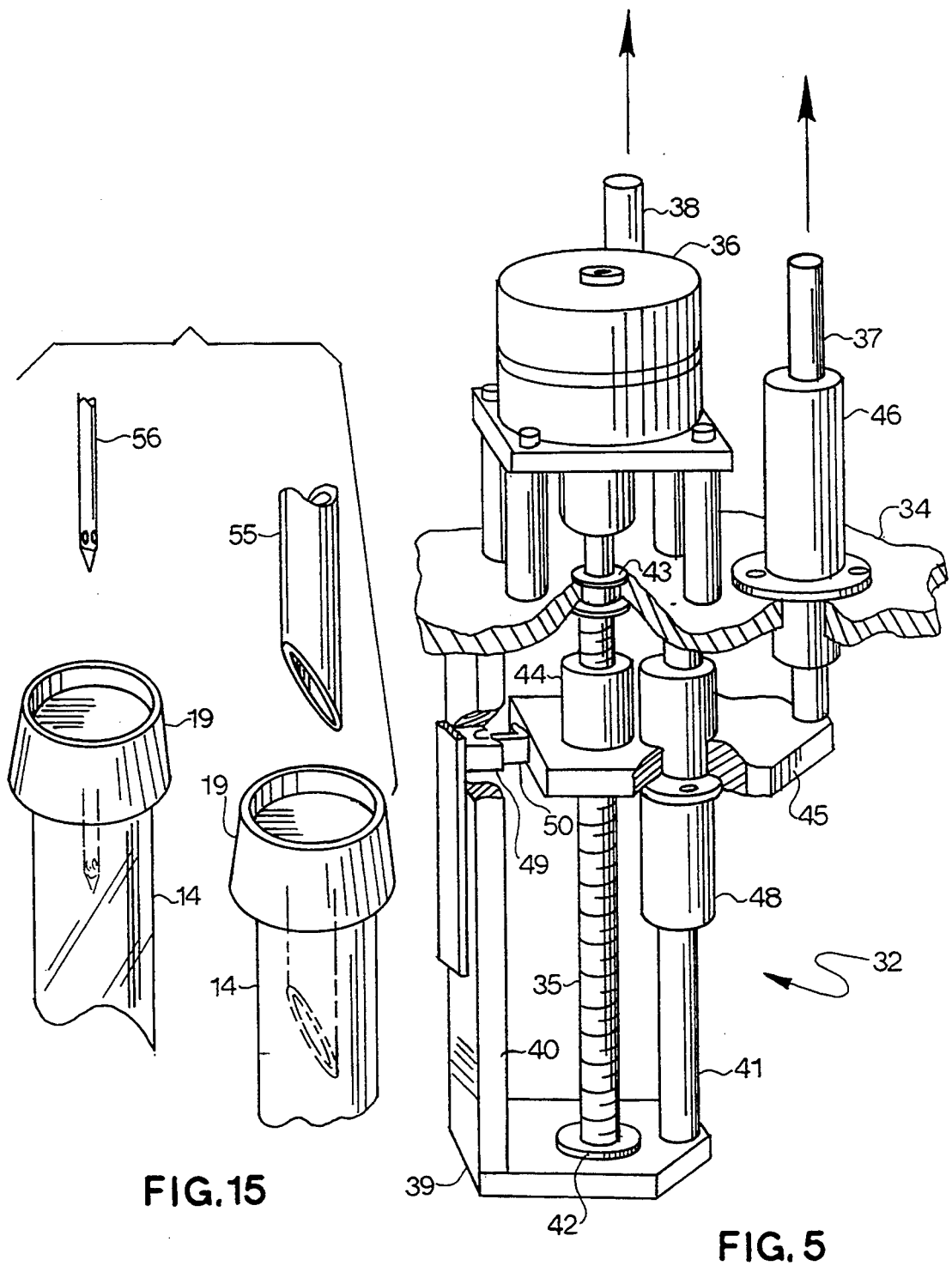
FIG. 5 is a side elevation view of the lifting mechanism for the waste removal assembly.
FIG. 15 is a side elevation view of the needle and the puncture tube proximate two sample containers, showing the relative displacement of the containers with respect to the needle and puncture tube. The needle and puncture tube appear above the containers in solid lines and in the containers in phantom lines after they have punctured through the stoppers.

The lift mechanism 32 (shown in FIG. 5) includes a horizontal plate 34 for fixedly securing the mechanism 32 to the base plate 11. It also includes a lead screw-type drive 35 powered by a motor 36 and used to move two plungers 37 and 38 vertically between a lowered and a raised position. A support frame 39, including an L-shaped member 40 and a guidepost 41 maintain the lead screw-type drive 35 in vertical and horizontal alignment, journaled between a bearing 42 secured to the bottom of the member 40 and a bearing 43 secured in an opening through the plate 34. A nut 44 mounted on the lead screw-type drive 35 moves vertically in response to the rotation of the drive; and a horizontally disposed connecting plate 45 secured to the nut 44 moves with it to drive the plungers 37 and 38.

To maintain the plungers 37 and 38 in vertical alignment, the mechanism 32 includes guide sleeves 46 and 47 (See FIG. 3) disposed vertically around the plungers 37 and 38, respectively, and fixedly secured to the horizontal plate 34. A third guide sleeve 48 disposed vertically around the post 41 and secured to the plate 45 maintains the plate 45 in horizontal alignment.

To control the movement of the nut 44 and, accordingly, the plungers 37 and 38, the system 10 includes electronic controls, including a top sensor 49 and a bottom sensor (not shown), which sense the presence of a contact 50 secured to the plate 45. Using the signal provided by these sensors, the electronic controls operate the motor 36 to move the nut 44 between upper and lower limits. The plungers 37 and 38 move from a lowered position where they lie below the bottom plate 20 of the transfer carousel 15 to a raised position.

Specifically, the plungers 37 and 38 move through openings 51 (See FIG. 3) formed in the plate 20 under each compartment 24, engage the bottom of platforms 25 disposed in two adjacent compartments 24, and drive the platforms upward along with the containers 14 which they support. Accordingly, the containers 14 move partially out of their respective compartments 24 and into engagement with the puncturing mechanism 33, as described below.

Figure 6:
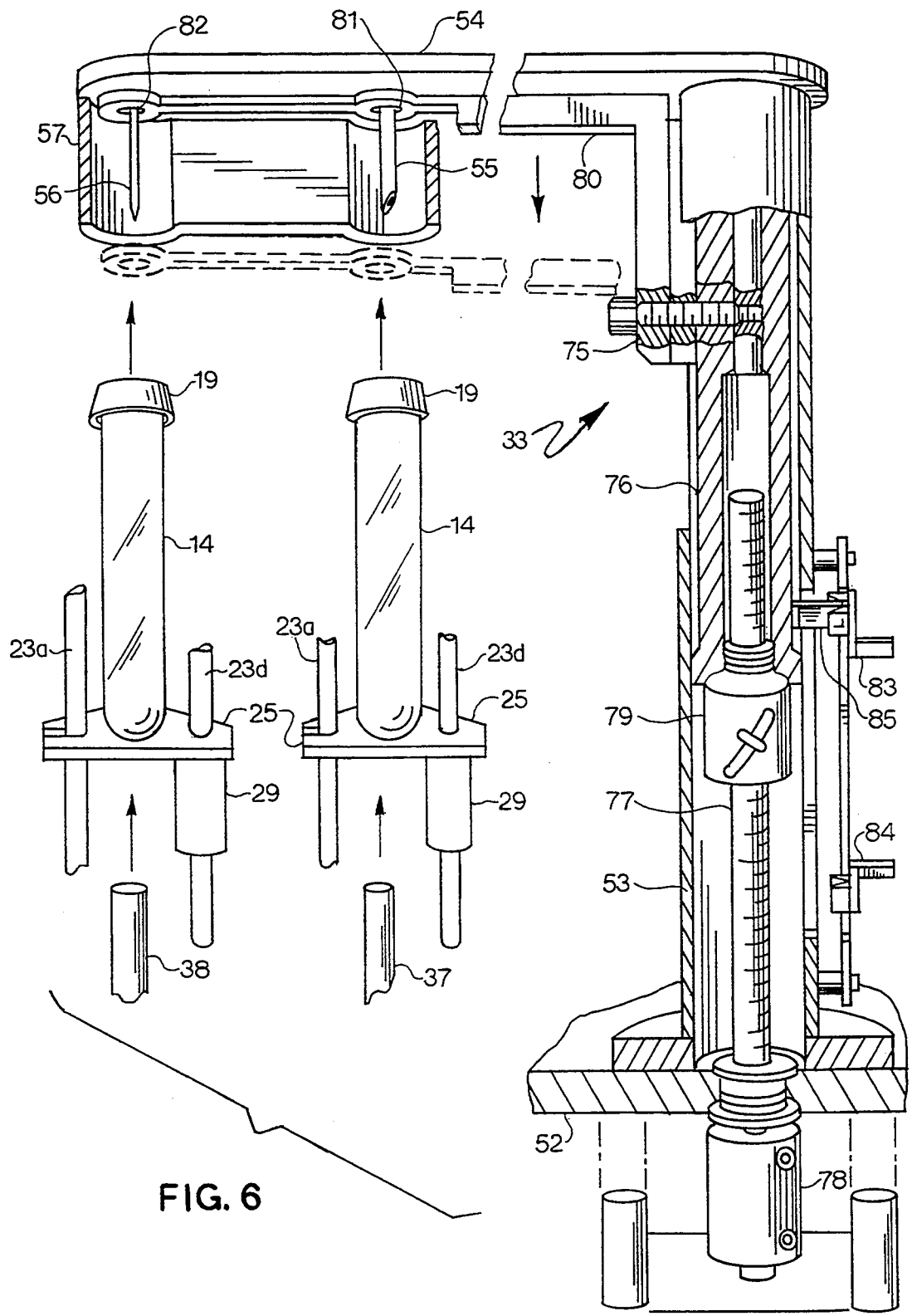
FIG. 6 is a side elevation view of the puncturing and stripper mechanisms with portions broken away to expose their construction. This figure also includes two sample containers disposed below the needle and the hollow puncture tube.

Turning now to FIG. 6, the puncturing mechanism 33 includes a securing plate 52 for attaching the mechanism 33 to the base plate 11 and a vertical support member 53 fixedly secured to the securing plate 52. The vertical member is a hollow tube made of metal or any other suitable material of high strength and rigidity. It supports a horizontal, cantilever member 54 fixedly secured to its top end. This horizontal support 54 supports a puncture tube 55 and a cleaning needle 56 in place at the first location 16.

The puncturing mechanism 33 also includes a transparent plastic shield 57 which extends around and downward of the member 54, secured to the bottom of this member. It shields the puncture tube 55 and the cleaning needle 56. It receives the tops of containers 14 and prevents the operator from touching the sharp ends of the puncture tube 55 and the needle 56, protecting the operator from injury.

The puncture tube 55 is a round and hollow, non-coring tube open at both ends and made of metal or any other suitable material. It lies disposed vertically and downwardly from the support member 54. A fitting releasably secures the tube 55 to the member 54; and the tube's central bore defines an opening 58 (See FIG. 4) which extends vertically through the member 54. The bottom end of the tube cuts an arcuate opening in the stopper and pushes the cut portion of the stopper to the side, thus forming a temporary opening through the stopper 19. Upon removal of the tube, the cut portion moves back in place; and the stopper reseals itself.

The bottom end of the puncture tube 55 (See FIG. 7–12) is bevelled and generally defines an oval face as shown in FIG. 8. This face is symmetric about its longitudinal center line and includes a heel portion H, a transition portion T disposed between the heel portion H and the transverse center line of the oval face, and a front portion F disposed between the transverse center line and the lowermost tip of the tube 55. The heel portion H is a semi-circular edge cut to a full radius and polished to a smooth finish. The transition portion varies from a semi-circular shape at the heel end to a flat shape at the transverse center line. Finally, the front portion F is flat; and two cut-out portions C sharpen the front tip to facilitate puncturing.

The angle a of the bevelled bottom end of the tube 55 and the configuration of the front portion F determine the force required for the tube 55 to puncture a stopper 19. By decreasing the angle a one may reduce the puncturing force. Moreover, by providing a sharp tip with the cut-outs C, one may further reduce the puncturing force. Thus, the front portion F allows quick and easy puncturing of a stopper 19 and movement of the tube 55 through the stopper.

While the front portion F allows easy movement of the tube 55 through a stopper 19, the heel portion H insures against coring of the stopper. As stated above, it has a smooth, round surface which does not cut the stopper 19. It merely pushes the cut portion downwardly and away from the tube 55.

By way of a specific example, a puncture tube 55 for use in a system 10 has a length of 1.500 inches obtained to a nominal tolerance specification of +0.000–0.005. It has an outside diameter of 0.134 inches +0.001—0.001 and an inside diameter of 0.114 inches +0.002—0.002. The angle a of the bevelled bottom end is 30°; and the angle b between the two lines of intersection formed by the cut-outs C and the flat front portion F of the bevelled face is 85°.

Figures 13, 14, 14A:
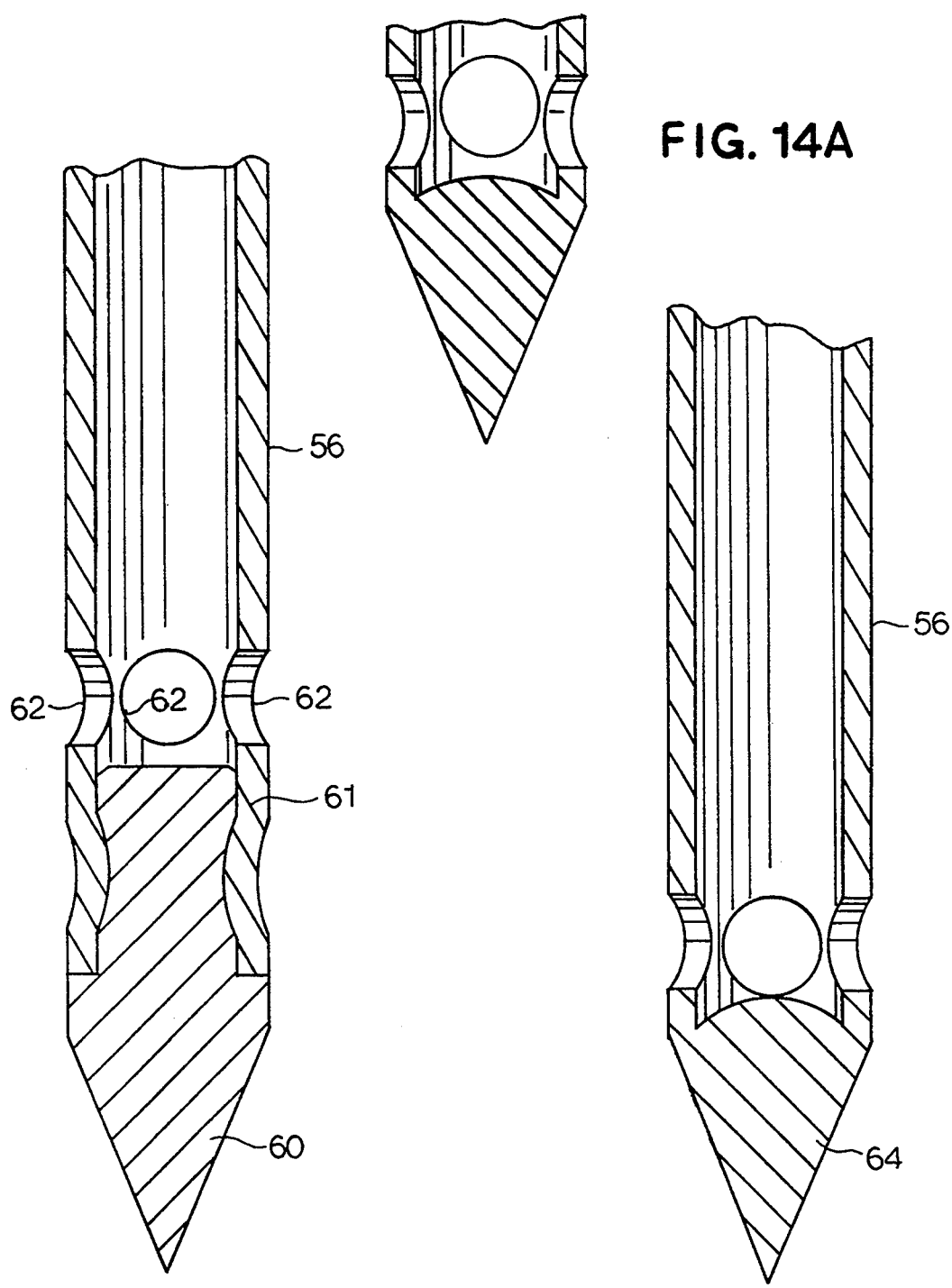
FIG. 13 is a partial cross-sectional view of the needle used in the waste removal assembly.
FIGS. 14 and 14A are partial cross-sectional views of two alternative embodiments of the waste removal needle.

The needle 56 also lies vertically and downwardly from the support member 54. It extends through an opening (not shown) in the member 54; and a fitting 59 (See FIG. 4) removably secures the needle, with a threaded connection (or other similar connection), to the member 54. The needle 56 is a hollow, round tube made of metal or any other suitable material. It has an outer diameter substantially smaller than the diameter of puncture tube 55 (e.g., 0.084 inches). Its top (first) end lies above member 54 and its bottom (second) end lies below it. The bottom end (See FIG. 13) is a closed sharp tip formed by inserting a pre-machined tip section 60 into the bottom end of the needle's tube body 61. By pinching or welding the tube body 61 into the tip 60, one secures the tip 60 in place. Alternatively, the needle 56 may have a sharp, solid tip 64 integrally formed with the tube body 61 (See FIG. 14).

The needle 56 includes a first set of four, round openings 62 having axes which lie on the same plane, 90° apart. These openings 62 lie proximate the top end of the tip 60 to prevent debris from collecting between the bottom of the openings 62 and the top of the tip 60. With this opening configuration, the needle may establish communication with the area around the entire periphery of its penetrating end without weakening the body 61. Alternatively, the needle may have any other suitable opening configurations with one set or many sets of openings or with openings staggered around the needle at various distances from the tip of the needle and/or from each other.

At location 16, the puncture tube 55 lies above the plunger 37 and the needle 56 lies above the plunger 38. As stated above, these plungers drive containers 14 disposed in adjacent compartments 24. As the lift mechanism 32 lifts the containers 14 upwardly, the puncture tube 55 and needle 56 engage the stoppers 19 of the corresponding containers 14, move through the stoppers, and into the containers 14 (See FIG. 15).

The distance which the lift mechanism lifts the containers 14 and the length of the puncture tube 55 determine the lowermost position of the puncture tube 55 in the container 14. Similarly, the lifting distance and the length of the needle 56 determine the lowermost position of the needle 56. At the lowermost position, the bottom end of puncture tube 55 lies below the stopper 19, a substantial distance above the level of the sample in the container 14; and the lower end of needle 56 lies above the level of the sample in its corresponding container 14, proximate the bottom surface of stopper 19 with the openings 62 disposed below this surface.

Once the puncture tube 55 and the needle 56 have established communication with the insides of two adjacent containers 14, a boom assembly 65 (See FIG. 1) moves a probe 66 into the container 14 through the puncture tube 55. This probe 66 is a tube connected to a pump and reservoir (not shown); and it removes a predetermined amount of the sample from the container 14. The boom assembly then transfers the sample to the cuvettes 67 of a continuous cuvette belt located at a second location 68. Alternatively, the probe may be a sensor which takes a reading from the sample disposed in the container 14 or a dispenser for dispensing material into the container.

Figure 16:
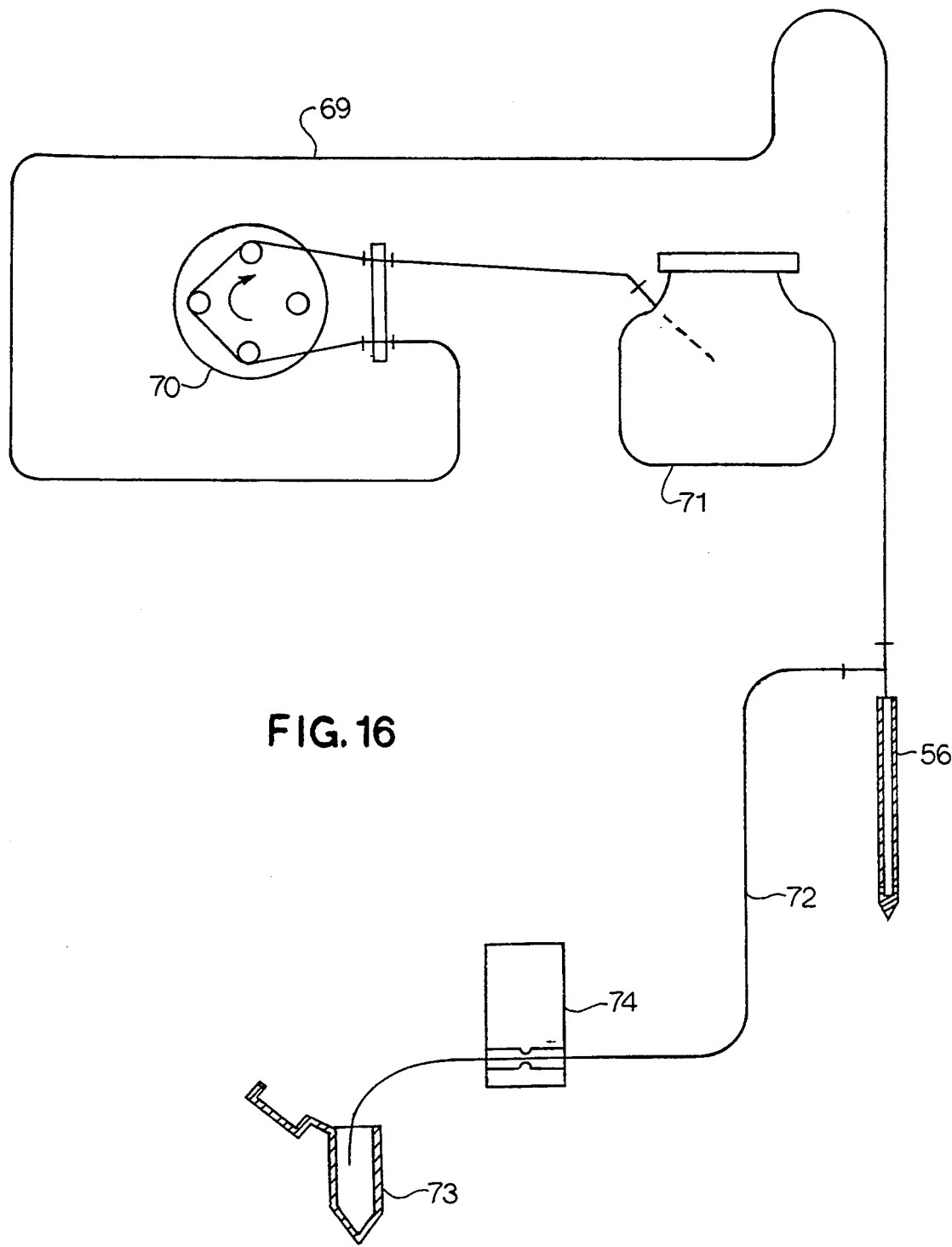
FIG. 16 is a schematic view of the pump and waste container used to evacuate the needle and the passageways and valves used to vent the needle to atmospheric pressure.

While the system 10 conducts sampling operations through the puncture tube 55, it also cleans the stopper 19 and surrounding area of the adjacent tube 14 with the needle 56. (See FIGS. 4 and 16) Tubing 69 connects the open top of the needle 56 to a pump 70 (e.g., a peristaltic pump) which activates when the lift mechanism 32 begins to raise the containers 14. The pump 70 continues to operate until the electronic controls of the system 10 deactivate it, after a predetermined time period.

While it operates, the pump 70 manipulates, i.e., decreases, the pressure and/or flow through the tubing 69 and the needle 56. Alternatively, the pump 70 may increase the pressure and/or flow. It removes debris and/or sample, e.g., blood serum, entrapped on the inside surface of the stopper 19 or otherwise displaces this waste away from the inside surface of the stopper and the surrounding inside surface of the container 14. It moves this waste through the openings 62 in the needle 56, through the needle 56 and the tubing 69, and into a waste container 71 for disposal. It does this by developing a negative pressure in the needle 56 and the tubing 69. The negative pressure that it develops must have an intensity sufficient to remove the waste but not the sample disposed generally at the bottom of the container 14.

After the pump 70 has stopped operating and drawing off waste, the system 10 vents the container 14 to atmosphere before withdrawing the needle 56. It does so through tubing 72 (See FIG. 16) which connects the top of the needle 56 with a waste container 73. A pinch valve 74 closes this tubing 72 until the system controls open the pinch valve and the tubing. This venting provides a rapid flow of air through the tubing 72 and the needle 56, and into the container 14. The negative pressure developed by the pump 70 in the container 14 causes this flow as venting occurs. The flow may provide additional flushing of any remaining sample and/or debris from the bottom of the stopper and the surrounding area into the container 14. Alternatively, the system 10 may include a pump or other similar device to enhance this flow.

After venting the container 14, the pinch valve 74 remains open and closes again when the system moves the next container in position for waste removal or displacement. In emergency situations, when a positive pressure develops in the container 14 and the pinch valve does not close, the tubing 72 receives any serum which flows out of the container 14 through the needle 56. This serum flows into a waste container 73 for disposal.

After removing waste from one container 14 and sampling an adjacent container 14, a stripper mechanism 75 (See FIG. 6) disposed in the vertical support 53 of the puncturing mechanism 33 strips the stoppers 19 from the puncture tube 55 and the needle 56 as the lift mechanism 32 lowers its plungers 37 and 38. This mechanism 75 disengages the containers 14 from the puncturing mechanism 33 and allows them to move back into the compartments 24.

To perform this function, the stripper mechanism 75 includes a tubular member 76 disposed in sliding engagement in the hollow support or housing 53. A lead screw-type drive 77 powered by a motor 78 drives the member 76 up and down using a nut 79 mounted for vertical movement on the lead screw-type drive 77 and secured to the bottom end of the member 76.

Secured at the top end of member 76, a push arm 80 extends through a vertical slot in the housing 53 and engages the stoppers 19. This push arm 80 has a flat configuration with a central opening 81 through which the puncture tube 55 extends and a central opening 82 through which the needle 56 extends. The push arm 80 applies constant downward pressure around the top of the stoppers 19 to lower the containers 14 downward.

To define the upper and lower limits of movement of the sliding member 76, the electronic controls of the system 10 include a top stripper assembly sensor 83 and a bottom stripper assembly sensor 84 secured to the outside of the housing 53. These devices sense the presence of an optical flag 85. Suitable securing devices secure the optical flag 85 to the member 76; and the optical flag 85 extends through a vertical slot in the housing 53 to the outside of the housing 53 where the sensor 83 and 84 can detect it.

Using the signals provided by these sensors, the system's electronic controls operate the motor 78 to move the nut 79, and thus the push arm 80 between predetermined upper and lower limits. The stripper mechanism moves this push arm 80 from a raised position proximate the horizontal support member 54 of the puncturing mechanism 33 to a lower position below the bottom end of the puncture tube 55 and the needle 56 and then back up again.

After the stripper mechanism 33 disengages the containers 14 from the puncture tube 55 and the needle 56, and, along with the lift mechanism, lowers the container in the compartments 24, the drive (not shown) of the transfer carousel 15 rotates the carousel 15 and moves a new container 14 under the needle 56; it moves the container 14 previously disposed under the needle 56 to a position below the puncture tube 55; and it moves the sample container 14 previously disposed in the position under the tube 55 toward the unloading carousel 17. The system repeats the above procedures; sampling and waste removal continue; and the system 10 transfers the spent containers 14 from the transfer carousel 15 to the unloading carousel 17.

The system 10 performs the cleaning and sampling functions simultaneously for two adjacent containers 14. It then moves the two containers and performs sampling in the container it has just cleaned and cleaning in a new container. However, one skilled in this art may modify the system so that it may separately perform the waste removal operation in one container at one station, move this container over to another station, and then perform the sampling operation.

While the above description and the drawings illustrate one preferred embodiment, one should understand, of course, that the invention is not limited to this embodiment. Those skilled in the art to which the invention pertains may make modifications and other embodiments employing the principles of this invention particularly upon considering the foregoing teachings. For example, one skilled in the art may use a drive mechanism to lower the puncture tube and needle rather than use a lift mechanism to raise the containers. The applicants, therefore, by the appended claims, intend to cover any modifications and other embodiments as incorporate those features which constitute the essential features of this invention.

What is claimed is:

1. An automated cleaning assembly for, prior to sampling, removing material from a top inner portion of an elongate sample container which has an open top and a closure means for normally closing the open top, said assembly comprising: a movable holding means for holding the container and moving it generally horizontally to a predetermined location; an elongate needle member disposed at said predetermined location, said member defining an elongate bore, at least one inlet opening proximate a first end, and an outlet opening, said needle member being closed and sharpened at the distal portion of said first end; driving means for providing relative, generally vertical displacement between the container and the needle member, said driving means providing the force for moving the sharpened end of the needle member through the closure means into the container and placing the distal end of the needle member proximate the closure means; a waste enclosure; tube means for connecting the needle member with the waste enclosure; and pump means communicating with the needle member for varying the pressure in the bore of the needle member and displacing the material from the top inner portion of the container through the tube means and into the waste enclosure.

2. The automated assembly of claim 1, further comprising a stripping means for disengaging said needle member from said container.

3. The automated assembly of claim 1, wherein said needle member is stationary and said driving means includes a lift means for moving said container against said needle member.

4. The automated assembly of claim 1, wherein said openings in needle member defines a plurality of inlet openings, said inlet openings being arranged in rows around said needle member in staggered relation.

5. The automated assembly of claim 1, further comprising venting means connected to said needle member for venting said container.

6. An automated cleaning assembly for removing material from a top inner portion of an elongate sample container which has an open top and a closure means for normally closing the open top, said assembly comprising: movable container transfer means for holding the container and moving it generally horizontally to a predetermined location; an elongate needle member disposed at said predetermined location, said member defining an elongate bore, at least one inlet opening proximate a first end, and an outlet opening, said needle member being closed and sharpened at the distal portion of said first end; driving means for providing relative, generally vertical, displacement between the container and the needle member after the movable container transfer means has moved the container to the predetermined location, said driving means providing the force for moving a penetrating end portion of the needle member into the container; and venting means connected to the needle member for venting the container after the needle member has established communication with the top inner portion of the container; said venting means including a waste enclosure and at least one tube for connecting the waste enclosure to the needle member.

* * * * *